United States Patent
Hastings

(10) Patent No.: US 9,113,605 B2
(45) Date of Patent: *Aug. 25, 2015

(54) METHODS AND COMPOSITIONS TO AGGREGATE ALGAE

(75) Inventor: Karin L. Hastings, Buckeye, AZ (US)

(73) Assignee: CORE INTELLECTUAL PROPERTIES HOLDINGS, LLC, Goodyear, AZ (US)

( * ) Notice: Subject to any disclaimer, the term of this patent is extended or adjusted under 35 U.S.C. 154(b) by 941 days.

This patent is subject to a terminal disclaimer.

(21) Appl. No.: 13/115,975

(22) Filed: May 25, 2011

(65) Prior Publication Data

US 2011/0253623 A1 Oct. 20, 2011

Related U.S. Application Data

(63) Continuation-in-part of application No. 12/927,619, filed on Nov. 19, 2010, now Pat. No. 8,574,887.

(60) Provisional application No. 61/281,707, filed on Nov. 20, 2009.

(51) Int. Cl.
| | | |
|---|---|---|
| *A01G 33/00* | (2006.01) | |
| *C12N 1/02* | (2006.01) | |
| *C12N 1/12* | (2006.01) | |
| *C12P 39/00* | (2006.01) | |

(52) U.S. Cl.
CPC ........ *A01G 33/00* (2013.01); *C12N 1/02* (2013.01); *C12N 1/12* (2013.01); *C12P 39/00* (2013.01)

(58) Field of Classification Search
CPC ....................................................... C12P 39/00
See application file for complete search history.

(56) References Cited

U.S. PATENT DOCUMENTS

| | | |
|---|---|---|
| 3,645,040 A | 2/1972 | Ort |
| 4,675,114 A | 6/1987 | Zagyvai et al. |
| 2011/0124089 A1 | 5/2011 | Stepenoff et al. |

OTHER PUBLICATIONS

Shelef et al., Microalgae Harvesting and Processing: A literature Review, Solar Energy Research Institute, Aug. 1984.*
Lee et al., Microbial flocculation, a potentially low-cost harvesting technique for marine microalgae for the production of biodiesel, J. Appl. Phycol, 21:559-567, Dec. 12, 2008.*
Oh et al., Harvesting of *Chlorella vulgaris* using bioflocculant from *Paenibacillus* sp. AM49, Biotechnology Letters 23:1229-1234, 2001.*
Helfrich et al., Clearing Muddy Pond Waters, Virginia Cooperative Extension, May 2009.*
Gong et al., Culture Conditions for Flocculant Production by *Paenibacillus polymyxa* BY-28, Journal of Environmental Science and Health, Part A, vol. A38, No. 4, pp. 657-669, 2003.*
Yang et al., Culture Medium and Grading Culture Technics for Bioflocculant Production by *Paenbacillus polymyxa* GA1, Environmental Science, vol. 27, No. 7, Jul. 2006.*
International Search Report and Written Opinion issued Nov. 23, 2011 for PCT/US2011/038006 filed May 25, 2011 (Inventor—Karin L. Hastings // Applicant—Mineral Biosciences LLC) (11 pages).
Yoon JH, et al., (2003) *Paenibacillus kribbensis* sp. nov. and *Paenibacillus terrae* sp. nov., bioflocculants for efficient harvesting of algal cells. International Journal of Systematic and Evolutionary Microbiology. 53: 295•301.
Kryder LR. (2007) Microalgae for Wastewater Treatment and Reuse. Available at http://www.leslieconsulting.com/docs/MicroalgaeForWastewaterTreatmentAndReuse.pdf (10 pages).

* cited by examiner

*Primary Examiner* — Taeyoon Kim
*Assistant Examiner* — Srikanth Patury
(74) *Attorney, Agent, or Firm* — Ballard Spahr LLP

(57) ABSTRACT

The present invention comprises methods and compositions for aggregating algae so as to separate the algal cells from an aqueous algae suspension. A bioflocculent, comprising a composition comprising a bacteria, is used to aggregate the algae.

8 Claims, No Drawings

SEQUENCE LISTING

<160> NUMBER OF SEQ ID NOS: 1

<210> SEQ ID NO 1
<211> LENGTH: 305
<212> TYPE: DNA
<213> ORGANISM: Artificial Sequence
<220> FEATURE:
<223> OTHER INFORMATION: Description of Artificial Sequence: Note =
Synthetic Construct

```
<400> SEQUENCE: 1
cttttcctgc atgggagaag gaggaaagrc ggagcaatct gtcacttgtg gatgggcctg      60
cggcgcatta gctagttggt ggggtaawgg cctaccaagg cgacgatgcg tagccgacct     120
gagagggtga tcggccacac tgggactgag acacggccca gactcctacg ggaggcagca     180
gtagggaatc ttccgcaatg ggcgaaagcc tgacggagca acgccgcgtg agtgatgaag     240
gttttcggat cgtaaagctc tgttgccagg gaagaacgtc ttgtagagta actgctacaa     300 gwkkg                                                                 305
```

METHODS AND COMPOSITIONS TO AGGREGATE ALGAE

RELATED APPLICATIONS

This application claims the priority of U.S. patent application Ser. No. 12/927,619, filed Nov. 19, 2010, which claims the priority of U.S. Provisional Patent Application Ser. No. 61/281,707, filed Nov. 20, 2009.

FIELD OF THE INVENTION

This invention relates to algae cultivation systems, and more specifically to methods and compositions for concentrating algae from a water source using a biological flocculent. The present invention minimizes harm to the algae.

BACKGROUND

Cultivation of microalgae, single-celled algal organisms, has been pursued for many years. Microalgae are unicellular organisms which produce oxygen by photosynthesis. Over 100,000 species of microalgae are known and new uses of them are being found continuously. Microalgae have a high growth rate and tolerance for varying environmental conditions. The large-scale cultivation of algae in open ponds presents some formidable challenges including the harvesting of the biomass grown in the ponds. For photosynthetic microorganisms, the ratio of biomass-to-liquid media may be very low, sometimes on a scale of only a few milligrams of biomass per liter. Accordingly, the costs associated with separating the biomass from the liquid media may be prohibitively expensive.

Microalgae have uses in the production of vitamins, pharmaceuticals, natural dyes, as a source of fatty acids, proteins and other biochemicals. Factors derived from microalgae have also been claimed to prevent neurodegenerative diseases and macular degeneration. They have been shown to be effective in the biological control of agricultural pests; as soil conditioners and biofertilizers in agriculture; for the production of oxygen and removal of nitrogen, phosphorus and toxic substances in sewage treatment; and in the biodegradation of plastics. Microalgae have been used as a renewable biomass source for the production of a diesel fuel substitute (biodiesel) and for electricity generation.

Due to the wide range of uses of microalgae and microalgae-based products, an effective method of harvesting microalgae is essential. The effective separation of microalgae from water is a crucial step in this process. Those skilled in the art have sought ways to improve algae production methods, but methods for removing algae from a dilute solution in a large pond of water so as to concentrate or aggregate the microalgae are needed. Conventional methods for harvesting microalgae are centrifugation, sedimentation, filtration under pressure through a microstrainer and flocculation with chemical flocculants. Filtration methods, centrifugation and strainer methods often damage the microalgal cells, preventing growth in smaller containers, use of the algae, or cause production of deleterious stress molecules or unwanted metabolic by-products. Flocculation with chemical flocculants contaminates the algal solution with chemicals that may interfere with later processes by the algae or treatment of the algae.

What is needed are methods and compositions that are effective in aggregating the algae growing in a container, such as industrial algal production ponds, that do not harm the algae. It would be desirable to provide a method for separation of microalgae from water that is less costly, easier to use, involves a lower energy consumption, provides a high yield and preserves the integrity of the cell structure, and enables retention of desirable cell components.

SUMMARY

The present invention comprises methods and compositions for aggregating algae growing in containers, for example, large containers such as industrial ponds, so that the algae harvested from one container and may be placed in a more concentrated amount in a second container, where the cells/mL is greatly increased over the original container.

The present invention comprises methods for obtaining concentrated biomass from an aqueous solution of microalgae, without causing the microalgae to be harmed significantly, such as ruptured. The present invention comprises a method comprising flocculation with a bioflocculent, removal of the microalgae from a container, such as an industrial containment system or a pond, and containment of the microalgae in a higher concentration in a smaller container. The invention is suitable for enterprises engaged in growing microalgae for all applications, including food, agricultural and pharmaceutical products. It can be adapted for specific species of bacteria and/or algae, if desired. The methods and compositions are less expensive and faster than currently available methods and aid in retention of many of the properties of the microalgae which may be damaged or lost in conventional separation technologies. The methods and compositions are simple to use and inexpensive to maintain.

An aspect of the invention comprises methods comprising flocculation of a microalgae suspension in a reservoir or container, for example, an industrial-sized pond, by application or provision of a bioflocculent. Flocculation of the algae may occur over several days, such as from one to six days, for one day, for two days, for three days, for four days, for five days, or for six days, referred to herein as a flocculation period. It is desired that during the flocculation period, the algae are not exposed to extreme hypoxic situations or complete loss of exposure to light, as the algae settle to the lower regions of the container. One skilled in the art can determine the time for adequate flocculation by monitoring the condition of the algae during the flocculation period to maintain good care of the algae. The bioflocculent may be one or more strains of bacteria that may or may not be specific for one or more species of algae. The flocculated suspension of algal cells may be removed via pumping or other removal methods to a smaller container, where the number of algal cells per milliliter of fluid is much greater than was the concentration of algal cells in the original container or reservoir. The present invention is suitable for use with many species of microalgae, and preserves the intact structure of the cells.

These and other advantages of the invention will be apparent to those skilled in the art from the following detailed description thereof.

DETAILED DESCRIPTION

The present invention comprises methods and compositions for concentration of algal populations. The present invention comprises methods and compositions for flocculating microalgae by application of a bioflocculent comprising a novel isolated strain of *Paenibacillus polymyxa*, Strain 2. Strain 2 was isolated by Global Organics, LLC of Goodyear, Arizona and deposited with ATCC, Accession No. PTA-12841 on Apr. 19, 2012.

A method of the present invention comprises the steps of flocculation and aggregation of the algae, and removal of the aggregated algae to a second container where the concentration of the algae is higher than was the concentration of algae in the first container. An aspect of the invention comprises methods comprising flocculation of a microalgae suspension in a reservoir or container, for example, an industrial-sized pond, by application or provision of a bioflocculent. Flocculation of the algae may occur over several days, such as from one to six days, for one day, for two days, for three days, for four days, for five days, or for six days, referred to herein as a flocculation period. It is desired that during the flocculation period, the algae are not exposed to extreme hypoxic situations or complete loss of exposure to light, as the algae settle to the lower regions of the container. One skilled in the art can determine the time for adequate flocculation by monitoring the condition of the algae during the flocculation period to maintain good care of the algae. The bioflocculent may be one or more strains of bacteria that may or may not be specific for one or more species of algae. The flocculated suspension of algal cells may be removed via pumping or other removal methods to a smaller container, where the number of algal cells per milliliter of fluid is much greater than was the concentration of algal cells in the original container or reservoir. The present invention is suitable for use with many species of microalgae, and preserves the intact structure of the cells.

As used herein algae or microalgae comprise single-celled microorganisms recognized to be algae.

As used herein flocculation is the process by which microalgae of microscopic size, suspended in a liquid medium, form stable aggregates. The algae aggregates settle downwards in the media solution and tend to accumulate in the lower regions of the container.

After flocculation has proceeded for a desired time period, the flocculation period, the fluid media in the upper regions of the container has a lower to almost zero concentration of algae. The upper region fluid media may be removed from the container, such as by pumping or draining the fluid. The media fluid in the lower region of the container, which contains a high concentration of algae cells per mL of fluid, may be removed by pumping or draining A container may also have a drain or exit port in a lower region of the container such that the lower region media fluid comprising the highly concentrated alga (flocculated), may be removed from the container without removing the upper region fluid. The pH of the pond can range from about 6.0 to about 11.0 for flocculation to occur.

An aspect of the invention comprises methods comprising flocculation of a microalgae suspension in a reservoir, for example, an industrial-sized pond, by application or provision of a bioflocculent. Flocculation of the algae may occur over a time period in which a majority of the algae are removed from the upper region of the water column of the container and are found in the lower regions or bottom of the container. The bioflocculent may be applied one time to the surface of the container, or may be applied more than one time if desired to increase the amount of algae aggregated. Additionally, one or more bioflocculents may be applied to the upper region of water that was removed from the container, which has a low to no concentration of algae, to aggregate any remaining algae. A bioflocculent of the present invention comprises a composition comprising *Paenibacillus polymyxa* Strain 2.

Provided herein are exemplary methods for production of biomass from flocculated algae using a bioflocculent comprising a *Paenibacillus polymyxa* bacteria composition having bioflocculation properties. A composition of the present invention comprises a *Paenibacillus polymyxa* strain, referred to as Strain 2, having a 16S ribosomal RNA sequence corresponding to SEQ. ID. NO. 1, and using a composition comprising Strain 2 and applying Strain 2 to an algae cultivation system comprising microalgae, and harvesting the biomass of microalgae. The algae cultivation system may include an aqueous environment, wherein the aqueous environment includes seawater and/or freshwater. The aqueous environment may be in a photobioreactor, a pond, or a vessel, or any container capable of containing fluid, media and algae.

SEQ ID NO. 1, is the DNA sequence of 16S RNA, from *Paenibacillus polymyxa* Strain 2, as isolated by Global Organics LLC, and deposited at ATCC, Accession No. PTA-12841 on Apr. 19, 2012, (American Type Culture Collection, 10801 University Boulevard, Manassas, Va., 20110).

```
                                    SEQ ID NO 1
CTTTTCCTGC ATGGGAGAAG GAGGAAAGRC GGAGCAATCT

GTCACTTGTG GATGGGCCTG CGGCGCATTA GCTAGTTGGT

GGGGTAAWGG CCTACCAAGG CGACGATGCG TAGCCGACCT

GAGAGGGTGA TCGGCCACAC TGGGACTGAG ACACGGCCCA

GACTCCTACG GGAGGCAGCA GTAGGGAATC TTCCGCAATG

GGCGAAAGCC TGACGGAGCA ACGCCGCGTG AGTGATGAAG

GTTTTCGGAT CGTAAAGCTC TGTTGCCAGG GAAGAACGTC

TTGTAGAGTA ACTGCTACAA GWKKG
```

*Paenibacillus polymyxa* Strain 2 shows a growth pattern different from other *P. polymyxa* strains isolated by Global Organics LLC. For example, PDA, (Potato Dextrose Agar) was used to grow two strains of *Paenibacillus polymyxa* that were isolated by Global Organics LLC. Strain 2 is very thick and slimy, whereas Strain 5 is very slimy and thin. Strain 5 does not function as a bioflocculent for the same types of algae that are flocculated or aggregated by Strain 2. For example, Strain 2, applied in spore form, will flocculate or aggregate at least algae of the *Chlorella, Scenedesmus, Nannochloris, Chlamydomonas, Chlorococcum, Cryptomonas, Microactinium*, and *Ellipsoidion* genera. Strain 5 does not flocculate or aggregate these species as does Strain 2.

The present invention comprises compositions comprising strains of bacteria having flocculation properties for flocculating algae. According to aspect of the invention, a *Paenibacillus polymyxa* strain, Strain 2, comprises a 16S ribosomal RNA sequence corresponding to SEQ. ID. NO. 1. In another embodiment, the 16S ribosomal RNA sequence is at least ninety-nine percent (99%) similar to the 16S ribosomal RNA sequence shown in SEQ. ID. NO. 1.

The bioflocculent may be applied to the container of algae. The bioflocculent, for example Strain 2, is provided as a stock solution, for example in a concentration range of about from $10^8$ to about $10^{12}$ cells/mL, from about $10^8$, from about $10^9$, from about $10^{10}$, from about $10^{11}$, from about $10^{12}$, and ranges therebetween, and may be diluted before adding to an algae container.

The bioflocculent bacteria applied to the container of algae, such as a pond, may be in a spore form when applied. It is theorized that the spores remain in a stationary phase in the water because no additional nutrients are added to the water. The bacteria applied to the container of algae, such as a pond, may be in a vegetative state when applied, that is, in the process of activated spores or as in reproducing bacillus. As used herein, bacteria may refer to a spore form or a vegetative form of a particular strain of bacteria, and may also be referred to as the bioflocculent bacteria.

The bioflocculent bacteria may be applied to the surface of the algae container by any method known to those skilled in the art, including, but not limited to, spraying or sprinkling. The bioflocculent bacteria may be injected or provided into the water column of the algae container at any level. An aspect of the present invention comprises spraying *Paenibacillus polymyxa* Strain 2 on the surface of an algae containing pond, wherein the algae concentration in the untreated pond, prior to application of the bacteria, is in a range of about $100 \times 10^4$ to about $100 \times 10^8$, or at about $100 \times 10^4$, $100 \times 10^5$, $100 \times 10^6$, $100 \times 10^7$, $100 \times 10^8$, and ranges thereinbetween. The biomass produced by the flocculation of the algae by the bacteria may be harvested by the biomass settling to at or near the bottom of the algae cultivation system, and then removal of the biomass to a second container or to a use of the algae.

Algae of the present invention may be cultured by methods known to those skilled in the art. For example, an algae container of the present invention may include one or more strains of microalgae. Such one or more strains of algae may be started from an initial, small amount of pure unialgal (virtually free from unwanted contaminant organisms) algal isolate. Such an inoculum may be generated in a controlled environment, such as in a laboratory or in a closed system. The isolate or isolates are expanded in number and placed in increasing larger containers until a concentration is reached that is used for the algae production container, such as a pond. In the algae production container, one or more strains or types of algae are grown in water with media providing nutrients for the algae, and light energy, such as sunlight. Other parameters such as pH are kept within acceptable ranges. The basic elements typically required for algal growth may include carbon, oxygen, hydrogen, nitrogen, sulfur, phosphorous, potassium, magnesium, iron and traces of several other elements.

The nutrients for algal growth may be contained in the water, supplied subsequently in dilution waters, or supplied independently of the dilution waters, in a concentration sufficient to allow the algae to grow and reach a desired density. The amount of nutrients needed to yield a desired algal density may be determined by the cell quota for that nutrient. That is, by the percent of the algal dry mass that is comprised of the element contained in the nutrient. The inverse of the cell quota is called the algae growth potential for that nutrient or element. For instance, if the desired final density is 1 gram/liter and if the algal type under consideration contains ten percent (10%) nitrogen in its biomass (i.e., a cell quota of 0.1), then the initial concentration of the atomic nitrogen in the culture should be at least 0.1 gram/liter. The same calculation may be performed for all nutrients to establish their initial concentration in the culture. Formulations of media for algal growth are known by those skilled in the art. An algal culture media may be diluted at different amounts depending on the size container. For example, 1:200 to 1:300 for 15 mL tubes, 1:400 to 1:600 for all intermediate steps up to the ponds, and 1:5,000 to 15,000 dilution at the pond level.

An aspect of the invention comprises providing light to the algae. The time-averaged light intensity to which an algal culture may be exposed may be adjusted by changes in the mixing intensity and/or in the optical depth of the pond. The optical depth in open ponds may be the depth of the pond. In open ponds, the temperature may be controlled by adjusting culture depth. After a time, an algal culture may reach a productive operating density depending on light intensity, temperature, and the starting inoculum size.

A method of the present invention comprises growing algae in water with algal media and nutrients in a first container while exposing the aqueous suspension to sunlight, to make an algal culture of a particular concentration. The size of the container may vary from laboratory scale to a 60,000 gallon pond. A method comprises adding a composition comprising a suspension of bioflocculent bacteria, such as *Paenibacillus polymyxa* Strain 2 in a spore form to an algal culture. The addition of media and nutrients to the algal culture are discontinued about the time, either before, at the same time of addition, or just after, when the bioflocculent is added to the algal culture. Admixing the aqueous solution of the bioflocculent bacteria to the algal culture to yield an algal-bacterial aqueous solution and continuing to expose the algal—bacterial aqueous solution to sunlight while the algal flocculate and concentrate at the bottom of the container; and, concentrating algae from the bottom of the container 12 to 120 hours after the bioflocculent bacteria is admixed with the aqueous solution of algae. Once the desired amount of algae have been removed from the water column, the water overlaying the flocculated algae is removed and the flocculated algae is pumped from the container. With this method, the algae are not harmed and maintain viability during the flocculation and harvesting.

Using *Paenibacillus polymyxa* Strain 2, not all species of algae may be flocculated. The algae which are not aggregated by the Strain 2 bioflocculent, and which remain in the water column, retain their viability and function normally.

A result of the algal system of the invention is that the bacteria appear to improve the quality of byproducts produced during processing of the concentrated algae. Such byproducts include increased lipid production and increased native protein yields. The capital cost of concentrating alga using this bioflocculent is small compared to established industry standards, and the operational cost of concentrating the algae is small compared to established industry standards.

The present invention comprises methods for the separation of microalgae from an aqueous suspension of microalgae, while maintaining the integrity of the cell structure, comprising, a) adding to an aqueous suspension of microalgae a bioflocculating bacteria, causing flocculation of at least some of the microalgae cells; and b) removing at least a portion of the liquid of the suspension. The method comprises use of a composition comprising a bioflocculating bacteria that is *Paenibacillus polymyxa* Strain 2, which is in spore form when added to the microalgae suspension. The method comprises flocculation of algae in the microalgae suspension wherein at least some of the microalgae flocculated are from the genera of *Chlorella, Scenedesmus, Nannochloris, Chlamydomonas, Chlorococcum, Cryptomonas, Microactinium* or *Ellipsoidion*. The time for flocculating, the flocculation period is at least 2 days, is at least 4 days, is 5 days. The method further comprises before a), discontinuing providing additional nutrient media to the suspension of algae. The method comprises a microalgae suspension that is contained in a pond of at least 60,000 gallons. The method comprises wherein the bioflocculating bacteria is added by spraying or sprinkling the bacteria on the surface of the microalgae suspension. The method may further comprise c) removing the flocculated algae. The method can comprise performing step b first or performing step c) first, followed by step b).

The present invention contemplates that other types of flocculent material, such as chemical flocculents or polymers, or co-flocculents such as calcium chloride as are known in the art could be used with the bioflocculent methods disclosed herein.

The following example is provided by way of description, and not limitation, of the invention.

EXAMPLES

Example 1

*Paenibacillus polymyxa* Strain 2 was grown and allowed to sporulate. The spores were stored at a concentration of $10^8$ to $10^{12}$ cells per mL. Strain 2 is a novel isolate and has not been genetically modified, but the present invention contemplates that genetically modified bacteria can be used if such modified bacteria are bioflocculents. *Paenibacillus polymyxa* Strain 2 has several characteristics that make it beneficial in the compositions and methods of the present invention, namely, it was not predatory to the algae of the algae culture, and it was a facultative anaerobic bacteria. During the flocculation period, it appeared that the algae maintained normal growth, respiration, and other physiological and physical properties in the presence of the bacteria.

Algae were grown in water and nutrient media in a 70,000 gallon pond which was twenty-two feet wide and 200 feet long. The depth of the pond was in the range of twelve to forty-eight inches. The size and depth of a pond can vary as desired; however, a depth greater than forty-eight inches is not preferred because the amount of sunlight reaching the bottom of the pond diminishes with depth. In particular, one of the advantages of the algae is that it can be grown and harvested at commercial scale, i.e., in tanks with a capacity of 5,000 to 1 million gallons or more, such as ponds of at least 60,000 gallon size.

A pump circulated water in the pond. The inlet to the pump was located in one side of the pond beneath the surface of the water in the pond. The inlet was near the bottom of the pond. The outlet through which water was returned to the pond was located above, at, or below the surface of water in the pond. Water left the pond through the inlet, passed through the pump, and returned to the pond at the outlet. Water entering the pond through the outlet generated circulation of at least some of the water in the pond. Multiple inlets and outlets can, if desired, be provided. The capacity of the pump can vary as desired, but was in the range of 100 to 200 gallons per minute. The purpose of the pump was not to create great turbulence in water in the pond, but was to promote a low, gradual circulation of water in the pond. Excessive turbulence can injure the algae. The pump ordinarily ran during daylight hours and not during the night. Additionally, one or two paddle wheels were continuously stirring the pond water. Aeration methods may be used in a pond, such as a bubble system of ambient air mixed with carbon dioxide, or carbon dioxide alone.

The surface of the water in the pond was open to ambient air and was exposed to sunlight during the day. If desired, a transparent cover can be provided for the pond. The daytime ambient temperature was in the range of 70 degrees F. to 110 degrees F., but was preferably in the range of 80 degrees F. to 95 degrees F., The temperature of the water in the pond was in the range of 60 degrees to 100 degrees F., preferably in the range of 70 degrees to 95 degrees F. Unicellular, not filamentous fresh water algae from the *Chlorella, Scenedesmus, Nannochloris, Chlamydomonas, Chlorococcum, Cryptomonas, Microactinium*, and *Ellipsoidion* genera were grown. Algae from other genera may be used in the present invention. Nutrients were added to the algae culture water to feed the algae. The nutritional composition ordinarily was in a liquid form and was added periodically to water in the pond, such as continuously fed into water in the pond at a rate in the range of 200 to 400 gallons per day. The compositions of nutrients for algae are well known and, by way of example, typically include 6% to 15% by weight nitrogen, 5% to 35% by weight phosphate, and 1% to 6% by weight potassium. About 200 to 400 gallons of algal nutrients were added to the 70,000 gallon pond each day. About 100 to 2500 gallons of water was added to the pond each 70,000 gallon pond each day to compensate for water lost into the atmosphere by evaporation.

The algae were allowed to grow in the pond until the algae concentration was between $0.25 \times 10^6$ cells/mL to over 1 million cells per mL. This aqueous algal concentration when dried generally produced algae solids that were 0.4% to 0.9% by weight of the aqueous algal concentration.

A desired concentration of algae in the pond was achieved, when the algae concentration was about $0.5 \times 10^6$ cells/mL and when the majority of the cells were in growth phase. The resulting flocculated algae was about $100 \times 10^6$ cells/mL. If flocculated again, the concentration of algae can be doubled.

200 to 500 gallons of the aqueous *Paenibacillus polymyxa* Strain 2 bacteria solution were added to the water in the algae pond. This original bacteria concentrate was about $10^{10}$, but it may vary from $10^8$ to $10^{12}$ cells/mL. $1:100 \times 1:240 = 1:24,000$ dilution of bacteria concentrate was added to the pond of algae.

The *Paenibacillus polymyxa* Strain 2 bacteria solution was dispersed on the entire pond surface using a sprinkler system. As soon as the bacteria solution was added to water in the 70,000 gallon pond, the algal nutritional composition was no longer added to water in the pond. After the *Paenibacillus polymyxa* Strain 2 bacteria spores were added to the 70,000 gallon pond, the bacteria spores function as biological flocculent by, it is theorized, attaching to algae and sinking to the bottom of the pond along with the algae. It is not desirable to wait for more than 5 days to harvest the algae from the bottom of the pond because once the algae are on the bottom of the pond they are shielded from sunlight, and, because the addition of nutrients to the pond was discontinued when the bacteria were added, the algae were no longer being fed.

The pH of the water in the 70,000 gallon pond during the initial growth of the algae and after the aqueous bacterial suspension is added to the pond is 7 to 12, preferably 8 to 11, and most preferably 7.5 to 10.5.

The genera or type of algae in the 70,000 gallon pond that was aggregated by the bioflocculent, such as *Paenibacillus polymyxa* Strain 2 and removed varied depending on strain of bacteria and type or genera of algae. Other strains of *Paenibacillus polymyxa*, such as Strain 5, do not function as bioflocculents of the eight bacteria listed above. See Example 3 for algae that do or do not flocculate. If desired, bioflocculent bacteria can be added to the pond on more than one occasion.

An advantage of the invention is that the algae remained viable during harvest and after they were harvested. The water was decanted from the 70,000 gallon pond, and an algae and bacteria composition was left behind in the pond container. The algae and bacteria composition was substantially comprised of viable algae. The algae and bacteria composition was removed using a mechanical system that does not break apart or harm the algae or lyse the algal cells. When the mechanical means was used, care was taken to not apply more than 100 gravities or excessive heat and pressure during harvesting of the algae and bacteria composition. For example, a temperature in excess of 212 degrees F. was not applied to the algae and a pressure not in excess of 250 psi was not applied to the algae. After the algae were removed from the bottom of the container, further mechanical concentration by centrifugation or other means can be performed to remove water and increase the algae concentration. During such further mechanical centrifugation, it is important to maintain the viability of the algae. By way of example and not limitation, one mechanical means that can be used to remove agglomerated algae from the bottom of the container is to use a slow running pump and filtration system that would suction agglomerated algae from the bottom of the container at a rate in the range of 2 to 10 gallons per minute.

Example 2

In the Example, eight algae types were tested for flocculation by five different strains of *Paenibacillus*, shown below as 2, 3, 81, 82 and 86. Strain 2 is *Paenibacillus polymyxa* Strain 2 as disclosed herein. On Day 1, the algae concentration in suspension was measured, and the noted strain of *Paenibacillus* was added in an effective amount. One Day 2, the cells on the bottom of the vessel were tested for cell concentration. In general, only Strain 2 was a bioflocculent.

| Date | Global Organics LLC Strain # | *C. vulgaris* presence | Algae density ($10^6$ c/mL) |
|---|---|---|---|
| Day 1 | 2 | + | 1.847 |
| | 3 | + | 1.847 |
| | 81 | + | 1.847 |
| | 82 | + | 1.847 |
| | 86 | + | 1.847 |
| Day 2 | 2 | + | 2.030 |
| | 3 | + | 0.057 |
| | 81 | + | 0.185 |
| | 82 | + | 0.466 |
| | 86 | − | 0 |
| Day 3 | 2 | + | 3.502 |
| | 3 | − | 0 |
| | 81 | − | 0 |
| | 82 | − | 0 |
| | 86 | − | 0 |
| Day 4 | 2 | + | 7.190 |
| | 3 | − | 0 |
| | 81 | − | 0 |
| | 82 | − | 0 |
| | 86 | − | 0 |
| Day 5 | 2 | + | 10.345 |
| | 3 | − | 0 |
| | 81 | − | 0 |
| | 82 | − | 0 |
| | 86 | − | 0 |
| Day 6 | 2 | + | 11.946 |
| | 3 | − | 0 |
| | 81 | − | 0 |
| | 82 | − | 0 |
| | 86 | − | 0 |
| Day 7 | 2 | + | 9.358 |
| | 3 | − | 0 |
| | 81 | − | 0 |
| | 82 | − | 0 |
| | 86 | − | 0 |

| Date | Global Organics LLC Strain # | *S. dimorphus* presence | Algae density ($10^6$ c/mL) |
|---|---|---|---|
| Day 1 | 2 | + | 0.976 |
| | 3 | + | 0.976 |
| | 81 | + | 0.976 |
| | 82 | + | 0.976 |
| | 86 | + | 0.976 |
| Day 2 | 2 | + | 1.063 |
| | 3 | − | 0 |
| | 81 | + | 0.030 |
| | 82 | + | 0.042 |
| | 86 | − | 0 |
| Day 3 | 2 | + | 3.088 |
| | 3 | − | 0 |
| | 81 | − | 0 |
| | 82 | + | 0.004 |
| | 86 | − | 0 |
| Day 4 | 2 | + | 5.353 |
| | 3 | − | 0 |
| | 81 | − | 0 |
| | 82 | − | 0 |
| | 86 | − | 0 |
| Day 5 | 2 | + | 13.394 |
| | 3 | − | 0 |
| | 81 | − | 0 |
| | 82 | − | 0 |
| | 86 | − | 0 |
| Day 6 | 2 | + | 18.217 |
| | 3 | − | 0 |
| | 81 | − | 0 |
| | 82 | − | 0 |
| | 86 | − | 0 |
| Day 7 | 2 | + | 18.380 |
| | 3 | − | 0 |
| | 81 | − | 0 |
| | 82 | − | 0 |
| | 86 | − | 0 |

| Date | Global Organics LLC Strain # | *C. moewusii* presence | Algae density ($10^6$ c/mL) |
|---|---|---|---|
| Day 1 | 2 | + | 1.003 |
| | 3 | + | 1.003 |
| | 81 | + | 1.003 |
| | 82 | + | 1.003 |
| | 86 | + | 1.003 |
| Day 2 | 2 | + | 3.001 |
| | 3 | − | 0 |
| | 81 | − | 0 |
| | 82 | + | 0.302 |
| | 86 | − | 0 |
| Day 3 | 2 | + | 4.913 |
| | 3 | − | 0 |
| | 81 | − | 0 |
| | 82 | + | 0.018 |
| | 86 | − | 0 |
| Day 4 | 2 | + | 4.857 |
| | 3 | − | 0 |
| | 81 | − | 0 |
| | 82 | − | 0 |
| | 86 | − | 0 |
| Day 5 | 2 | + | 5.982 |
| | 3 | − | 0 |
| | 81 | − | 0 |
| | 82 | − | 0 |
| | 86 | − | 0 |
| Day 6 | 2 | + | 5.283 |
| | 3 | − | 0 |
| | 81 | − | 0 |
| | 82 | − | 0 |
| | 86 | − | 0 |
| Day 7 | 2 | + | 5.555 |
| | 3 | − | 0 |
| | 81 | − | 0 |
| | 82 | − | 0 |
| | 86 | − | 0 |

| Date | Global Organics LLC Strain # | *S. obliquus* presence | Algae density ($10^6$ c/mL) |
|---|---|---|---|
| Day 1 | 2 | + | 0.777 |
| | 3 | + | 0.777 |
| | 81 | + | 0.777 |
| | 82 | + | 0.777 |
| | 86 | + | 0.777 |

| Date | Global Organics LLC Strain # | *S. obliquus* presence | Algae density ($10^6$ c/mL) |
|---|---|---|---|
| Day 2 | 2 | + | 1.847 |
| | 3 | − | 0 |
| | 81 | + | 0.207 |
| | 82 | + | 0.945 |
| | 86 | − | 0 |
| Day 3 | 2 | + | 6.769 |
| | 3 | − | 0 |
| | 81 | − | 0 |
| | 82 | + | 0.004 |
| | 86 | − | 0 |
| Day 4 | 2 | + | 10.947 |
| | 3 | − | 0 |
| | 81 | − | 0 |
| | 82 | − | 0 |
| | 86 | − | 0 |
| Day 5 | 2 | + | 12.282 |
| | 3 | − | 0 |
| | 81 | − | 0 |
| | 82 | − | 0 |
| | 86 | − | 0 |
| Day 6 | 2 | + | 12.589 |
| | 3 | − | 0 |
| | 81 | − | 0 |
| | 82 | − | 0 |
| | 86 | − | 0 |
| Day 7 | 2 | + | 8.502 |
| | 3 | − | 0 |
| | 81 | − | 0 |
| | 82 | − | 0 |
| | 86 | − | 0 |

| Date | Global Organics LLC Strain # | *C. sorokiniana* presence | Algae density ($10^6$ c/mL) |
|---|---|---|---|
| Day 1 | 2 | + | 1.389 |
| | 3 | + | 1.389 |
| | 81 | + | 1.389 |
| | 82 | + | 1.389 |
| | 86 | + | 1.389 |
| Day 2 | 2 | + | 3.226 |
| | 3 | − | 0 |
| | 81 | + | 0.745 |
| | 82 | + | 1.772 |
| | 86 | − | 0 |
| Day 3 | 2 | + | 1.769 |
| | 3 | − | 0 |
| | 81 | − | 0 |
| | 82 | + | 0.366 |
| | 86 | − | 0 |
| Day 4 | 2 | + | 1.987 |
| | 3 | − | 0 |
| | 81 | − | 0 |
| | 82 | − | 0 |
| | 86 | − | 0 |
| Day 5 | 2 | + | 7.222 |
| | 3 | − | 0 |
| | 81 | − | 0 |
| | 82 | − | 0 |
| | 86 | − | 0 |
| Day 6 | 2 | + | 13.082 |
| | 3 | − | 0 |
| | 81 | − | 0 |
| | 82 | − | 0 |
| | 86 | − | 0 |
| Day 7 | 2 | + | 17.254 |
| | 3 | − | 0 |
| | 81 | − | 0 |
| | 82 | − | 0 |
| | 86 | − | 0 |

| Date | Global Organics LLC Strain # | *Nannochloropsis* presence | Algae density ($10^6$ c/mL) |
|---|---|---|---|
| Day 1 | 2 | + | 0.589 |
| | 3 | + | 0.589 |
| | 81 | + | 0.589 |
| | 82 | + | 0.589 |
| | 86 | + | 0.589 |
| Day 2 | 2 | + | 2.007 |
| | 3 | − | 0 |
| | 81 | + | 0.03 |
| | 82 | + | 0.042 |
| | 86 | − | 0 |
| Day 3 | 2 | + | 10.769 |
| | 3 | − | 0 |
| | 81 | − | 0 |
| | 82 | + | 0.004 |
| | 86 | − | 0 |
| Day 4 | 2 | + | 10.947 |
| | 3 | − | 0 |
| | 81 | − | 0 |
| | 82 | − | 0 |
| | 86 | − | 0 |
| Day 5 | 2 | + | 10.282 |
| | 3 | − | 0 |
| | 81 | − | 0 |
| | 82 | − | 0 |
| | 86 | − | 0 |
| Day 6 | 2 | + | 11.589 |
| | 3 | − | 0 |
| | 81 | − | 0 |
| | 82 | − | 0 |
| | 86 | − | 0 |
| Day 7 | 2 | + | 9.875 |
| | 3 | − | 0 |
| | 81 | − | 0 |
| | 82 | − | 0 |
| | 86 | − | 0 |

| Date | Global Organics LLC Strain # | *Micractinium* presence | Algae density ($10^6$ c/mL) |
|---|---|---|---|
| Day 1 | 2 | + | 0.888 |
| | 3 | + | 0.888 |
| | 81 | + | 0.888 |
| | 82 | + | 0.888 |
| | 86 | + | 0.888 |
| Day 2 | 2 | + | 1.323 |
| | 3 | − | 0 |
| | 81 | + | 0.009 |
| | 82 | + | 0.030 |
| | 86 | − | 0 |
| Day 3 | 2 | + | 1.423 |
| | 3 | − | 0 |
| | 81 | − | 0 |
| | 82 | + | 0.010 |
| | 86 | − | 0 |
| Day 4 | 2 | + | 1.643 |
| | 3 | − | 0 |
| | 81 | − | 0 |
| | 82 | − | 0 |
| | 86 | − | 0 |
| Day 5 | 2 | + | 4.603 |
| | 3 | − | 0 |
| | 81 | − | 0 |
| | 82 | − | 0 |
| | 86 | − | 0 |
| Day 6 | 2 | + | 4.740 |
| | 3 | − | 0 |
| | 81 | − | 0 |
| | 82 | − | 0 |
| | 86 | − | 0 |
| Day 7 | 2 | + | 4.882 |
| | 3 | − | 0 |
| | 81 | − | 0 |
| | 82 | − | 0 |
| | 86 | − | 0 |

| Date | Global Organics LLC Strain # | *S. quadricauda* presence | Algae density ($10^6$ c/mL) |
|---|---|---|---|
| Day 1 | 2 | + | 2.223 |
| | 3 | + | 2.223 |
| | 81 | + | 2.223 |
| | 82 | + | 2.223 |
| | 86 | + | 2.223 |
| Day 2 | 2 | + | 1.989 |
| | 3 | − | 0 |
| | 81 | + | 0.016 |
| | 82 | + | 0.599 |
| | 86 | − | 0 |
| Day 3 | 2 | + | 3.309 |
| | 3 | − | 0 |
| | 81 | − | 0 |
| | 82 | + | 0.129 |
| | 86 | − | 0 |
| Day 4 | 2 | + | 7.947 |
| | 3 | − | 0 |
| | 81 | − | 0 |
| | 82 | − | 0 |
| | 86 | − | 0 |
| Day 5 | 2 | + | 10.356 |
| | 3 | − | 0 |
| | 81 | − | 0 |
| | 82 | − | 0 |
| | 86 | − | 0 |
| Day 6 | 2 | + | 10.351 |
| | 3 | − | 0 |
| | 81 | − | 0 |
| | 82 | − | 0 |
| | 86 | − | 0 |
| Day 27 | 2 | + | 12.502 |
| | 3 | − | 0 |
| | 81 | − | 0 |
| | 82 | − | 0 |
| | 86 | | 0 |

Example 3

Chlorophyta and Xanthophyta that have shown flocculation activity using the *Paenibacillus polymyxa* strain 2.

| | |
|---|---|
| *Actinastrum* | *hantzchii* |
| *Ankistrodesmus* | *falcatus* |
| *Botrycoccus* | *braunii* |
| *Chlorella* | *vulgaris* |
| *Chlorella* | *sorokiniana* |
| *Coelastrum* | *reticulum* |
| *Desmococcus* | *olivaceus* |
| *Desmodesmus* | *protuberans* |
| *Gloeocystis* | *bacillus* |
| *Golenkinia* | *radiata* |
| *Kirchneriella* | *obesa* |
| *Micractinium* | *pusillum* |
| *Oocystis* | *lacustris* |
| *Palmella* | *miniata* |
| *Pediastrum* | *duplex* |
| *Scenedesmus* | *quadricauda* |
| *Scenedesmus* | *obliquus* |
| *Scenedesmus* | *dimorphus* |
| *Selenastrum* | *capricornatum* |
| *Westella* | *botryoides* |
| *spirogyra* | *juergensii* |
| *Cosmocladium* | sp |
| *Closterium* | *acutum* |
| *Cosmarium* | *perissum* |
| *Closterium* | *closterioides* |
| *Closterium* | *navicula* |
| *Netrium* | *digitus* |
| *Netrium* | *oblongum* |
| *Cosmarium* | *contractum* |
| *Cosmarium* | *montrealense* |
| *Cosmarium* | *pseudoconnatum* |
| *Staurastrum* | *anatinum* |
| *Staurastrum* | *claviferum* |
| *Staurastrum* | *bioculatum* |
| *Euglena* | *caudata* |
| *Ellipsoidion* | *acuminatum* |
| *Nannochloropsis* | sp |
| *Nannochloropsis* | *oculata* |
| *Chlamydomonas* | sp |

Cyanobacteria that have shown low flocculation activity using the *Paenibacillus polymyxa* strain 2.

| | |
|---|---|
| *Geitleria* | sp |
| *Radiocystis* | sp |
| *Aphanothece* | sp |
| *Gloeothece* | sp |
| *Cyanobacterium* | sp |
| *Synechococcus* | sp |
| *Bacularia* | sp |
| *Cyanothece* | sp |
| *Johannesbaptista* | sp |
| *Aphanocapsa* | sp |
| *Woronichinia* | sp |
| *Gloeocapsa* | sp |
| *Eucapsis* | sp |
| *Chroococcus* | sp |
| *Chroococcidiopsis* | sp |
| *Myxosarcina* | sp |
| *Pseudanabaena* | sp |
| *Limnothrix* | sp |
| *Jaaginema* | sp |
| *Oscillatoria* | sp |
| *Glaucospira* | sp |
| *Spiritensis* | sp |
| *Planktolyngbya* | sp |
| *Homoeothrix* | sp |
| *Schizothrix* | sp |
| *Arthrospira* | sp |
| *Planktothrix* | sp |
| *Lyngbya* | sp |
| *Scytonema* | sp |
| *Hassallia* | sp |
| *Anabaena* | sp |
| *Nostoc* | sp |
| *Phytodinium* | sp |
| *Stylodinium* | sp |
| *Cryptomonas* | sp |

What is claimed is:

1. A method for the separation of microalgae from an aqueous suspension of microalgae, while maintaining the integrity of the microalgal cell structure, comprising,
   a) discontinuing providing additional nutrient media to the aqueous suspension of microalgae;
   b) adding to the aqueous suspension of microalgae a bioflocculating bacteria, causing flocculation of at least some of the microalgae cells, wherein the bioflocculating bacteria is *Paenbacillus polymyxa* Strain 2 deposited with the American Type Culture Collection (ATCC) under Accession Number PTA-12841; and
   c) removing at least a portion of the liquid of the suspension.

2. The method of claim 1, wherein the time for flocculating the microalgae is at least 2 days.

3. The method of claim 1, wherein the time for flocculating the microalgae is at least 4 days.

4. The method of claim 1, wherein the time for flocculating the microalgae is 5 days.

5. The method of claim 1, wherein the microalgae suspension is contained in a pond of at least 60,000 gallons.

6. The method of claim 1, wherein the bioflocculating bacteria is added by spraying or sprinkling the bacteria on the surface of the microalgae suspension.

7. The method of claim 1, further comprising d) removing the flocculated microalgae from the aqueous suspension of step b).

8. The method of claim 7, wherein steps c) and d) can be performed in any order.

* * * * *